(12) United States Patent
Yonezawa

(10) Patent No.: US 6,735,333 B1
(45) Date of Patent: May 11, 2004

(54) PATTERN INSPECTION APPARATUS

(75) Inventor: Eiji Yonezawa, Aichi (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/362,678

(22) Filed: Jul. 29, 1999

(30) Foreign Application Priority Data

Jul. 30, 1998 (JP) .......................................... 10-215920

(51) Int. Cl.$^7$ ................................................ G06K 9/00
(52) U.S. Cl. ................... 382/145; 382/152; 356/237.1; 356/237.2; 356/498
(58) Field of Search ................................ 382/141, 144, 382/145, 108, 149, 225, 152; 356/237, 432, 433, 124, 237.3, 239.2, 398, 237.1, 237.2, 446, 445, 603, 498, 337, 600, 601; 359/798, 11, 21–23

(56) References Cited

U.S. PATENT DOCUMENTS

| | | | |
|---|---|---|---|
| 5,003,615 A | * 3/1991 | Seitz | 382/108 |
| 5,572,598 A | * 11/1996 | Wihl | 382/144 |
| 5,812,259 A | * 9/1998 | Yoshino et al. | 356/237.3 |
| 5,828,500 A | * 10/1998 | Kida et al. | 359/798 |
| 5,847,822 A | * 12/1998 | Sugiura et al. | 356/239.2 |
| 5,880,838 A | * 3/1999 | Marx et al. | 356/498 |
| 5,889,593 A | * 3/1999 | Bareket | 356/445 |
| 6,148,097 A | * 11/2000 | Nakayama et al. | 382/141 |
| RE37,740 E | * 6/2002 | Chadwick et al. | 356/394 |

FOREIGN PATENT DOCUMENTS

| | | | |
|---|---|---|---|
| EP | 0 628 806 | 12/1994 | G01N/21/88 |
| JP | 7-27709 | 1/1995 | G01N/21/88 |
| JP | 10-144747 | 5/1998 | H01L/21/66 |

OTHER PUBLICATIONS

Patent Abstracts of Japan vol. 1997, No. 12, Dec. 25, 1997 & JP 09 203710 A (TOPCON CORP; TOSHIBA CORP) Aug. 5, 1997 *Abstract.

* cited by examiner

*Primary Examiner*—Jayanti K. Patel
*Assistant Examiner*—Sheela Chawan

(57) ABSTRACT

A pattern inspecting apparatus includes an illuminating optical system for illuminating a pattern in a region subject to inspection on a workpiece from a substantially perpendicular direction; a detecting optical system for detecting regularly reflected light or transmitted light from the pattern illuminated by the illuminating optical system, the detecting optical system having a numerical aperture which does not allow the structure of the pattern in the region subject to inspection to be optically resolved; a wavelength-varying system for selectively rendering variable the wavelength of the light detected by the detecting optical system; and a measuring system for measuring the structure of the pattern on the basis of light intensity information of the detected light in correspondence with the wavelength varied by the wavelength-varying system.

8 Claims, 3 Drawing Sheets

PATTERN INSPECTION APPARATUS

BACKGROUND OF THE INVENTION

The present invention relates to a pattern inspecting apparatus suitable for inspection of a pattern on a semiconductor wafer, liquid-crystal glass, or the like.

The inspection of the acceptability of a pattern formed on a semiconductor wafer is typically performed by using the following methods.

(a) The wafer is tilted at various angles while strong light is being applied to the wafer from a diagonal direction, and an inspector macroscopically inspects the wafer visually under dark-field observation. This macroscopic inspection is made by making use of the fact that the state of diffracted light from the pattern formed on the wafer subtly differs from the state of a non-defective unit.

(b) The wafer is macroscopically inspected by the inspector visually under bright-field observation by making use of diffused lighting which is larger than the wafer and by principally making use of regularly reflected light. This macroscopic inspection is also made by making use of the fact that the brightness and the color subtly differ from the state of a non-defective unit.

(c) The configuration of the pattern is microscopically inspected visually or automatically by using an optical microscope.

(d) The configuration of the pattern is inspected in detail in a pinpoint manner by using a scanning electron microscope.

However, according to the above-described inspection, the following problems have been encountered.

According to the methods (a) and (b), since inspection is performed visually by a human being, it is difficult to detect defects if the overall wafer surface is uniformly abnormal. In addition, the visual inspection by a human being can be performed at high speed, but there are variations in the inspection capability among inspectors and there are oversights, so that there is a drawback in ensuring stable and sufficient quality of inspection.

In the inspection (c) using the optical microscope, since it is a microscopic inspection, it takes excessive time in inspecting all the fine pattern. In addition, although line width of the pattern formed on the wafer has recently become very small, the inspection of a pattern which is finer than a limit of resolution in relation to the wavelength of light is virtually impossible with the optical microscope. Furthermore, in a case of inspection for a resist that passes light therethrough, since the configuration of the pattern cannot be observed clearly, inspection accuracy is poor.

In the inspection (d) using the scanning electron microscope, although measurement accuracy is high, since it is a pinpoint inspection, an enormously long time is required for inspecting an average line width and its distribution.

SUMMARY OF THE INVENTION

In view of the above-described background art, an object of the present invention is to provide an inspecting apparatus which is capable of macroscopically inspecting a step structure such as a fine pattern (the step referred to herein means a structure in which the phase of light reflected from or transmitted through this portion has a value different from the phase of the light of other portions) and of easily obtaining average information thereof.

To attain the above-described object, the present invention is characterized by comprising the following features.

(1) A pattern inspecting apparatus which inspects a pattern formed on a workpiece to be inspected, said apparatus comprising:
  an illuminating optical system which illuminates a pattern in a region subject to inspection on a workpiece in a substantially perpendicular direction;
  a detecting optical system which detects regularly reflected light or transmitted light from the pattern illuminated by the illuminating optical system, the detecting optical system having a numerical aperture which does not allow a structure of the pattern in the region subject to inspection to be optically resolved;
  a wavelength-varying system which selectively renders variable a wavelength of the light to be detected by the detecting optical system; and
  a measuring system which measures the structure of the pattern on the basis of light intensity information of the detected light in correspondence with the wavelength varied by the wavelength-varying system.

(2) The pattern inspecting apparatus as set forth in (1), wherein the wavelength-varying system is provided in the illuminating optical system to selectively vary a central wavelength to thereby provide illuminating light of a narrow band.

(3) The pattern inspecting apparatus as set forth in (1), wherein the illuminating optical system emits illuminating light of a wide band, and the wavelength-varying system is provided in the detecting optical system to selectively vary a central wavelength so that the detecting optical system detects light of a narrow band.

(4) The pattern inspecting apparatus as set forth in (1), wherein the light intensity information represents intensity characteristic of interfering light in relation to varied wavelength, the interfering light is caused by light from a pattern portion in the region subject to inspection and by light from the rest in the region subject to inspection, and the measuring system obtains an average characteristic parameter regarding the structure of the pattern on the basis of the intensity characteristic of interfering light.

(5) The pattern inspecting apparatus as set forth in (4), wherein the parameter relates to an average area ratio of the pattern portion in the region subject to inspection, an average area ratio of the rest in the region subject to inspection, or a line width of the pattern in the region subject to inspection.

(6) The pattern inspecting apparatus as set forth in (4), wherein the parameter is obtained on the basis of a periodicity of a changed waveform and an amplitude thereof in the intensity characteristic of interfering light obtained by varying the wave length.

(7) The pattern inspecting apparatus as set forth in (4), further comprising:
  a storage device which stores therein standard intensity characteristics of interfering light obtained respectively from a non-defective workpiece and a defective workpiece;
  wherein the parameter is obtained on the basis of a degree of similarity with respect to the standard intensity characteristic stored in the storage device.

(8) The pattern inspecting apparatus as set forth in (1), further comprising:
  a storage device which stores therein a result of measurement on a standard workpiece;
  a judging system which judges whether or not the pattern in the region subject to inspection is defective upon comparison between the result of measurement stored in the storage device and a result of measurement on the pattern in the region subject to inspection.

(9) The pattern inspecting apparatus as set forth in (1), wherein the detecting optical system includes an imaging device which two-dimensionally images a substantially entire region of the workpiece or a specified region thereof required for inspection.

(10) A pattern inspecting apparatus which inspects a pattern formed on a workpiece to be inspected, said apparatus comprising:

an illuminating optical system having a lamp and a diffusion plate;

a detecting optical system having an imaging lens and an image pickup element, the image pickup element having a certain number of pixels which cannot optically resolve a fine pattern formed on the workpiece to be inspected;

a wavelength-varying system inserted into an optical path extending from the lamp to the image pickup element, the wavelength-varying system having a drive unit;

an image processor operatively connected to the detecting optical system; and a controller operatively connected to the drive unit and the image processor.

(11) The pattern inspecting apparatus as set forth in (10), wherein the wavelength-varying system varies light of a wide band to light of a narrow band by selectively varying a central wavelength.

(12) The pattern inspecting apparatus as set forth in (10), further comprising:

a storage device which stores therein a result of measurement on a standard workpiece and which is operatively connected to the image processor.

The present disclosure relates to the subject matter contained in Japanese patent application No. Hei. 10-215920 (filed on Jul. 30, 1998), which is expressly incorporated herein by reference in its entirety.

DESCRIPTION OF THE PREFERRED EMBODIMENT

Figure 1:
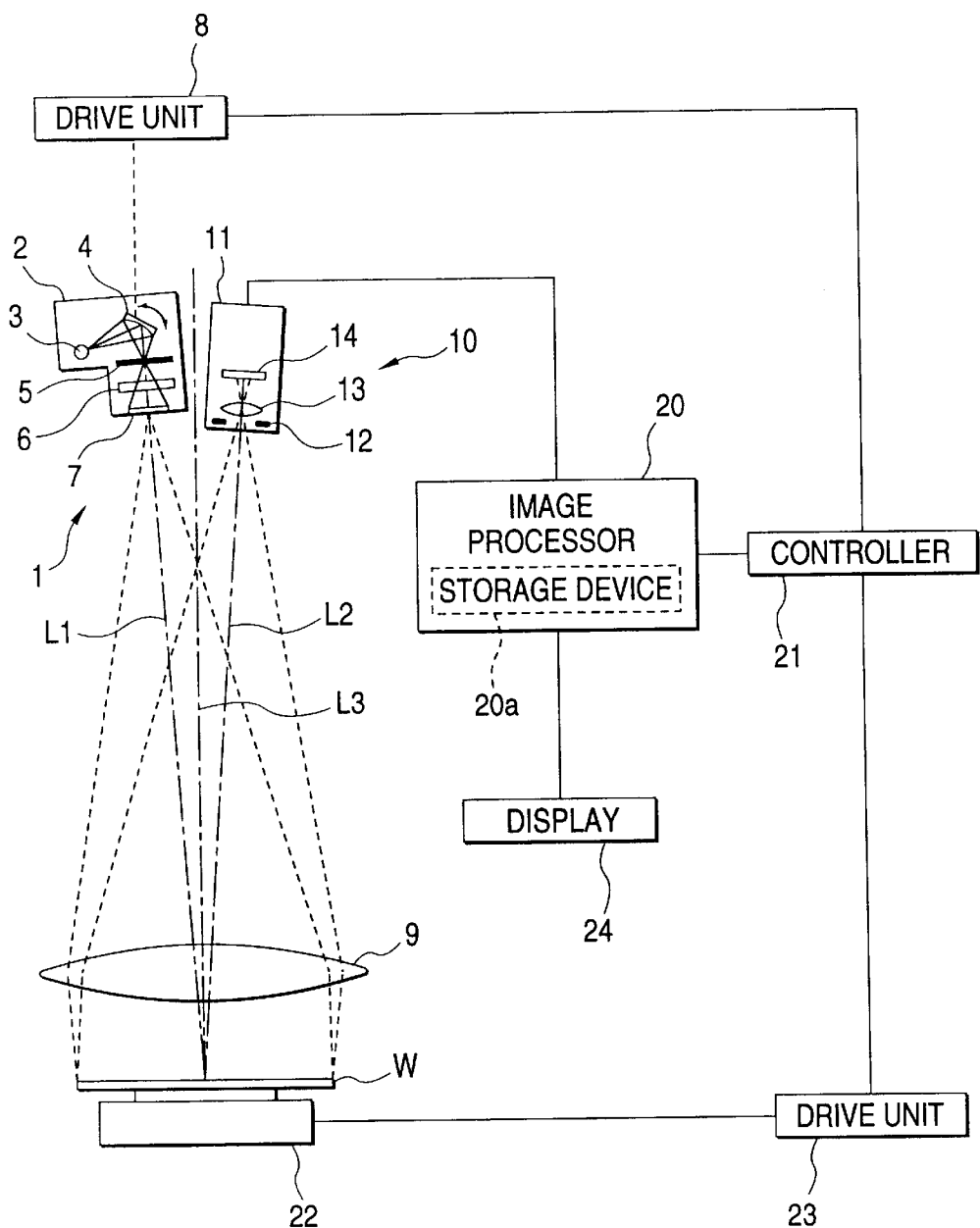
FIG. 1 is a diagram illustrating a schematic configuration of an inspecting apparatus in accordance with the present invention.

Hereafter, a description will be given of an embodiment of the present invention with reference to the drawings. FIG. 1 is a diagram illustrating a schematic configuration of an inspecting apparatus in accordance with the present invention.

Reference numeral 1 denotes an illuminating optical system for illuminating a wafer W which is an object to be inspected which is placed on an X-Y stage 22, and the illuminating optical system 1 has an illuminating unit 2 and a collimator lens 9 which is larger than the wafer W. Reference numeral 10 denotes a detecting optical system for detecting reflected light from the wafer W illuminated by the illuminating optical system 1, and the detecting optical system 10 has the collimator lens 9 used jointly by the illuminating optical system 1 and a CCD camera 11.

An optical axis L2 of the detecting optical system 10 is disposed in such a manner as to be symmetrical with an optical axis L1 of the illuminating optical system 1 about an optical axis L3 of the collimator lens 9, and the CCD camera 11 images an inspection surface of the wafer W by regularly reflected light from the wafer W illuminated by the illuminating optical system 1. The optical axis L1 is disposed in such a manner as to be inclined with respect to the optical axis L3 so as to illuminate the wafer W from a substantially perpendicular direction, as well as to avoid the interference between the illuminating unit 2 and the CCD camera 11. In this embodiment, an angle formed between the optical axis L3 and the optical axis L1 is set at 3 degrees. It should be noted an arrangement may be provided such that the wafer W is illuminated in the perpendicular direction by making the optical axis L3 and the optical axis L1 coincide with each other, and the inspection surface of the wafer W is imaged by regularly reflected light while avoiding interference between the illuminating unit 2 and the CCD camera 11 by also making the optical axis L2 coaxial by using a half mirror.

The illuminating unit 2 has a halogen lamp 3, i.e., a light source, a grating 4, an aperture 5 having a spot opening, and diffusion plates 6 and 7. The halogen lamp 3 emits light in a wide band whose spectral characteristic is known. The grating 4 is provided with a periodically uneven surface structure on a substrate having a concave surface, and of the light emitted from the halogen lamp 3, only narrow-band light having a particular central wavelength due to the diffraction by the grating 4 is selected so as to be focused at the opening of the aperture 5 and pass therethrough. Since the relationship between the central wavelength of the light diffracted by the grating 4 and its diffraction angle is in a known relationship, as the angle of inclination of the grating 4 is continuously changed by a drive unit 8, it is possible to select narrow-band light having a desired central wavelength. The light which passed through the aperture 5 is diffused by the two diffusion plates 6 and 7, and is converted to uniformly diffusive illuminating light having sufficiently uniform luminance. The diffusive illuminating light emergent from the diffusion plate 7 is converted to substantially parallel light by the collimator lens 9 and is then applied to the wafer W.

The regularly reflected light from the wafer W illuminated by the illuminating optical system 1 is collimated by the collimator lens 9, and an image of the substantially entire surface of the wafer W is formed on an imaging element 14 through a taking diaphragm 12 and a taking lens 13. This detecting optical system 10 is made an optical system having a sufficiently small numerical aperture so that a step structure of a fine pattern formed on the wafer W will not be optically resolved.

A video signal from the CCD camera 11 is inputted to an image processor 20. After the image processor 20 subjects the video signal from the CCD camera 11 to predetermined processing such as A/D conversion and the like, the image processor 20 performs necessary preprocessing such as noise removal and sensitivity correction of the imaging element and measures an average characteristic amount (the line width of the pattern and the like) of the step structure on the wafer W. Reference numeral 20a denotes a storage device provided in the image processor 20. Numeral 21 denotes a controller for controlling the respective devices. The controller 21 is connected to the drive unit 8 for changing the angle of inclination of the grating 4, to control the driving of the drive unit 8 for making variable the wavelength of the illuminating light for the wafer W at the time of image processing by the image processor 20.In addition, a drive unit 23 for the X-Y stage 22 is connected to the controller 21. Numeral 24 denotes a display, and an image fetched by the image processor 20 and inspection information are displayed thereon.

Next, a description will be given of the measurement of an average characteristic amount of the step structure on the pattern.

When a fine step structure portion of the pattern on the workpiece (object to be inspected) is macroscopically observed with a sufficiently small numerical aperture which does not allow the fine step structure to be optically resolved, phase components of the light reflected by (or transmitted through) the workpiece interfere with each other, so that the intensity of the light which is observed produces a change in relative intensity in correspondence with the observed wavelength (wavelength of the illuminating light). The changed waveform of an interference intensity corresponding to the wavelength at this time is determined by the average characteristic amount of the step structure. Accordingly, in the case where observation is made with a sufficiently small numerical aperture which does not allow the fine step structure to be optically resolved, it becomes possible to measure the average characteristic amount of the step structure by measuring the changed waveform of the interference intensity corresponding to the wavelength.

Figure 2:
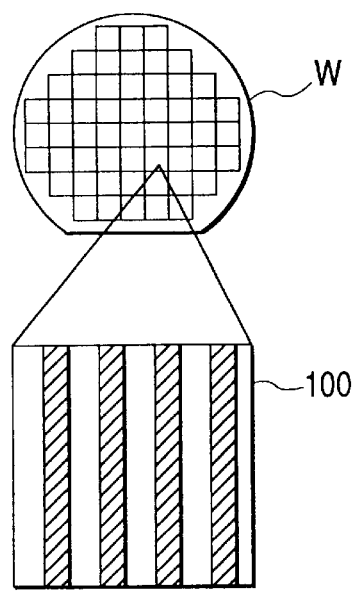
FIG. 2 is a diagram illustrating an example of the structure of fine pattern steps in an inspection region in a workpiece.

The basic principle of this measurement will be described. It is now assumed that observation is made with a sufficiently small numerical aperture which does not allow the fine step structure of the pattern in a small region 100 on the workpiece to be optically resolved (i.e., it is assumed that the CCD camera 11 in the embodiment shown in FIG. 1 does not have resolving power for the pattern in the small region 100). In FIG. 2, shaded portions show projecting step pattern portions, and white ground portions show portions where the pattern is not provided.

It is assumed that an electric field component of the light reflected (including the case of transmission; hereinafter the same) from a portion other than a step pattern is a, and that an electric field component of the light reflected from a top (a flat portion) of the step pattern is b. It should be noted that the light reflected from an inclined portion of the step pattern is ignored since its out put direction is completely different. Here, if it is assumed that the optical path difference at the step is h, and that the amount of phase shift produced in the reflection is α, that the amplitude of a is $k_1$, and that the amplitude of b is $k_2$, then a and b can be expressed by the following formulae:

$$a = k_1 \cos(\omega)$$ [Formulae 1]

$$b = k_2 \cos(\omega + 2\pi h/\lambda + \alpha)$$

Since the electric field c of the interfering light is c=a+b, the intensity C of the interfering light can be expressed as $$C = \frac{1}{2\pi} \int_0^{2\pi} c^2 \, d\omega = \frac{1}{2\pi} \int_0^{2\pi} (a+b)^2 \, d\omega = \frac{1}{2\pi} \int_0^{2\pi} a^2 \, d\omega + \quad \text{[Formula 2]}$$

$$\frac{1}{2\pi} \int_0^{2\pi} b^2 \, d\omega + \frac{1}{2\pi} \int_0^{2\pi} 2ab \, d\omega$$

$$= \frac{k_1^2}{2\pi} \int_0^{2\pi} \cos^2(\omega) \, d\omega + \frac{k_2^2}{2\pi} \int_0^{2\pi} \cos^2(\omega + 2\pi h/\lambda + \alpha) \, d\omega +$$

$$\frac{k_1 k_2}{2\pi} \int_0^{2\pi} 2\cos(\omega)\cos(\omega + 2\pi h/\lambda + \alpha) \, d\omega$$

$$= \frac{1}{2} k_1^2 + \frac{1}{2} k_2^2 + k_1 k_2 \cos(2\pi h/\lambda + \alpha)$$

$$= A + B + 2\sqrt{AB} \cos(2\pi h/\lambda + \alpha)$$

(A and B are intensities of a and b.)

Figure 3:
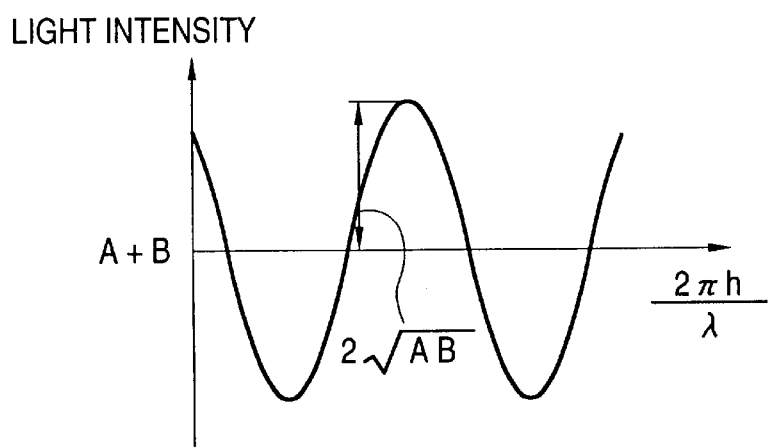
FIG. 3 is a diagram illustrating an example of a changed waveform of the interfering light intensity obtained by varying the wavelength.

From the above formulae, if the wavelength is varied, the intensity of the interfering light changes with the following amplitude by using A +B as the central level:

$$\text{amplitude} = 2\sqrt{AB}$$ [Formula 3]

so that wavelength characteristic information on the changed waveform can be obtained as shown in FIG. 3. Accordingly, if the central level and the amplitude of the changed waveform are measured, A and B can be measured.

Since A and B are proportional to an area ratio D of a portion where the pattern is not provided and an area ratio E of a top portion of the pattern, respectively, in the region subject to inspection, if k1 and k2 in D=A×k1

E=B×k2 are determined in advance by detailed measurement data, D and E (i.e., distributions of average area ratios of the portion where the pattern is not provided and the top portion of the pattern) can be determined from the above formulae. In addition, in a case where the pattern is linear, since its line width W is substantially proportional to E, if k3 in W=E×k3 is determined in advance, the line width W (average line width) can be determined.

Figure 4:
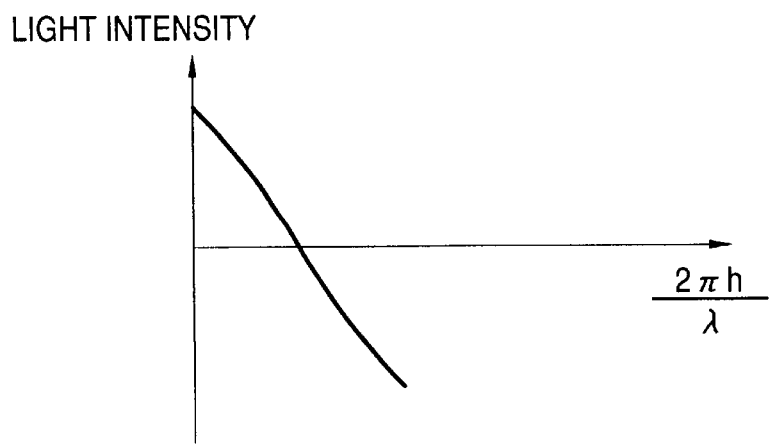
FIG. 4 is a diagram illustrating an example of a changed waveform of the interfering light intensity in a case where a pattern in which the step is smaller than an equal grade of the wavelength is an object to be inspected.

It should be noted that if a pattern in which the step is smaller than an equal grade of the wavelength is an object to be inspected, since the phase difference due to the difference in the step becomes small, there are cases where even if the wavelength is varied, a changed waveform having periodicity cannot be obtained, as shown in FIG. 4. In this case, it suffices if waveform characteristic information obtained from a standard non-defective workpiece and a standard defective workpiece (it is preferable to provide a plurality of standard stages for them) is stored in advance, comparison is then made between this information and the wavelength characteristic information obtained from the workpiece being inspected, and the aforementioned parameters D, E, and W representing the average characteristics of the step structure are determined by making use of the degree of its similarity (amount of deviation).

Although a description has been given above of the case of two bundles of rays a and b, in the case of three or more bundles of rays as well (e.g., in the case of a resist pattern, since the resist is semitransparent, the light which is transmitted through the pattern and is reflected from a boundary portion with a substrate is also added), the formulae become only complex, and measurement can be effected by the same principle.

Next, a description will be given of the inspection operation in accordance with this embodiment. By changing the angle of inclination of the grating 4 by the drive unit 8, the wavelength of the illuminating light from the illuminating unit 2 is selectively varied, and the wafer W placed on the X-Y stage 22 is thereby illuminated. The image processor 20 fetches image data of a plurality of wafers W (e.g., 20 pieces) which are imaged by the CCD camera 11 in synchronism with the wavelength selection of the illuminating light under control by the controller 21. In this embodiment, it is assumed that the practically entire surface of the wafer W can be imaged at one time, but imaging is effected by moving the X-Y stage 22 in a case where the wafer W is imaged in small divided units or in a case where a large-size wafer W is imaged.

From the plurality of pieces of image data fetched by varying the wavelength, the image processor 20 extracts the region of a circuit pattern subject to inspection which is set in advance, and determines the wavelength characteristic of the interfering light with respect to the wavelength change according to the above-described method from information on the luminance in that region. Since k1, k2, and k3 determined from the detailed measurement data on the same portion as the portion subject to inspection have been stored in the storage device 20a on the basis of the standard wafer, average parameters of the step structure (the area of the portion where the pattern is not provided, the area of the top portion of the pattern, and the line width) are obtained by performing arithmetic processing by using this data and the wavelength characteristic of the portion subject to inspection. It suffices if this processing is performed for each region of the necessary portion subject to inspection.

If the characteristics of the step structure of the region subject to inspection are thus obtained, since the values of the respective parameters concerning the same region as the region subject to inspection in the standard wafer (wafer with a non-defective pattern) are stored in the storage device 20a, the acceptability of the pattern is determined by comparing these values and the values of the respective parameters of the wafer W to be inspected (further, selection on the acceptability of the wafers can be effected automatically on the basis of these results). In addition, the results of measurement and the result of determination are displayed on the display 21 to allow the inspector to ascertain the state of distribution of the pattern.

Figure 5:
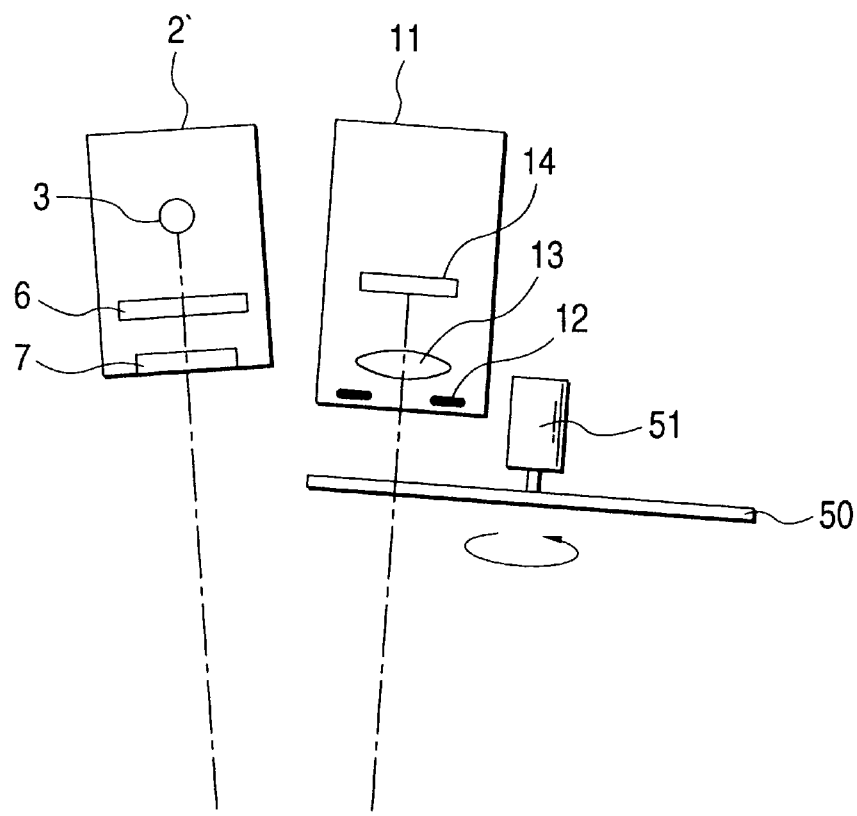
FIG. 5 is a diagram illustrating a modification of the embodiment.

Various modifications are possible for the above-described embodiment. Although in the foregoing embodiment the wavelength change is effected on the illuminating optical system 1 side, the wavelength change may be effected on the detecting optical system 10 side, as shown in FIG. 5. A wide band of light whose spectral characteristics are known is emitted from the halogen lamp 3 of an illuminating unit 2', is diffused by the diffusion plates 6 and 7, and is converted to diffused illuminating light with sufficiently uniform luminance. A rotating plate 50 having a plurality of narrow-band interference filters for selecting a wavelength necessary for measurement is disposed in front of the CCD camera 11 included in the detecting optical system 10, and the rotating plate 50 is rotated by a motor 51 to selectively insert a filter into the optical path. As a result, the CCD camera 11 is capable of imaging the wafer W by using the narrow-band light whose central wavelength is selectively varied. It should be noted that the method of selecting the wavelength by this rotating plate 50 may be effected on the illuminating optical system 1 side instead of the grating 4 shown in the foregoing embodiment.

As the configuration of the detecting optical system 10, in addition to detecting the inspection region by the CCD camera (two-dimensional area sensor) at one time in a two-dimensional manner, the detecting optical system 10 may be alternatively configured by adopting a scanning method using a line sensor or a method in which point-like detection is effected by a single sensor and the point-like detection (or the single sensor) is scanned for two-dimensionally. In these methods, even if the workpiece is large as in the case of a liquid-crystal substrate or the like, it is not necessary to use a large-size lens, and therefore it is possible to prevent an increase in the manufacturing cost. It should be noted that, even in the method of effecting point-like detection, overwhelmingly higher inspection can be performed as compared with the scanning electron microscope.

As described above, in accordance with the present invention, it is possible to easily obtain average characteristic information on the step structure irrespective of the limit of resolution concerning the step structure of a fine pattern.

In addition, since the inspection is a macroscopic inspection utilizing light, if the CCD camera or the like is used, it is possible to obtain the distribution of two-dimensional characteristics more easily, and high speed inspection can be performed.

What is claimed is:

1. A pattern inspecting apparatus which macroscopically inspects a fine pattern formed on a workpiece to be inspected, said apparatus comprising:
    an illuminating optical system which illuminates the pattern in a region subject to inspection on the workpiece in a substantially perpendicular direction;
    a detecting optical system which detects interfering light by reflected light or transmitted light from the pattern illuminated by the illuminating optical system, the detecting optical system having a sufficiently small numerical aperture which does not allow a structure of the pattern in the region subject to inspection to be optically resolved;
    a wavelength-varying system which selectively varies a central wavelength with a narrow-band among a plurality of different central wavelengths, the wavelength-varying system being disposed in the illumination optical system or the detecting optical system; and
    a measuring system which obtains an average characteristic parameter of the structure of the pattern on the basis of light intensity information of each detected interfering light in correspondence with each central wavelength.

2. The pattern inspecting apparatus as set for the in claim 1, wherein the wavelength-varying system is disposed in the illuminating optical system to selectively vary the central wavelength of illuminating light with the narrow band.

3. The pattern inspecting apparatus as set forth in claim 1, wherein the illuminating optical system emits illuminating light with a wide band, and the wavelength-varying system is disposed in the detecting optical system to selectively vary the central wavelength of the detected light with the narrow band.

4. The pattern inspecting apparatus as set forth in claim 1, wherein the average characteristic parameter relates to an average area ratio of the pattern portion in the region subject to inspection, an average area ratio of the rest in the region subject to inspection, or a line width of the pattern in the region subject to inspection.

5. The pattern inspecting apparatus as set forth in claim 1, wherein the average characteristic parameter is obtained on the basis of a periodicity of a changed waveform and an amplitude thereof in the light intensity information.

6. The pattern inspecting apparatus as set forth in claim 1, further comprising:

a storage device which stores therein standard light intensity informations obtained respectively form a non-defective workpiece and a defective workpiece;

wherein the average characteristic parameter is obtained on the basis of a degree of similarity with respect to the standard light intensity informations stored in the storage device.

7. The pattern inspecting apparatus as set forth in claim 1, further comprising:

a storage device which stores therein a result of measurement on a standard workpiece;

a judging system which judges whether or not the pattern in the region subject to inspection is defective upon comparison between the result of measurement stored in the storage device and a result of measurement on the pattern in the region subject to inspection.

8. The pattern inspecting apparatus as set for the in claim 1, wherein the detecting optical system includes an imaging device which two-dimensionally images a substantially entire region of the workpiece or a specified region thereof required for inspection.

\* \* \* \* \*